US006810103B1

United States Patent
Tybinkowski et al.

(10) Patent No.: US 6,810,103 B1
(45) Date of Patent: Oct. 26, 2004

(54) GANTRY FOR COMBINED TOMOGRAPHY SCANNER

(75) Inventors: Andrew P. Tybinkowski, Boxford, MA (US); Robert F. Riemer, Andover, MA (US); Ronald E. Swain, Reading, MA (US); Eric Bailey, Hampton, NH (US); Robert M. Williams, Wilmington, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/197,059

(22) Filed: Jul. 16, 2002

Related U.S. Application Data
(60) Provisional application No. 60/305,813, filed on Jul. 16, 2001.

(51) Int. Cl.[7] ................................................. A61B 6/00
(52) U.S. Cl. ......................... 378/20; 378/4; 250/363.04
(58) Field of Search ............................... 378/5, 15, 20; 5/601, 943; 250/363.04, 363.05

(56) References Cited

U.S. PATENT DOCUMENTS

| | | | |
|---|---|---|---|
| 4,797,008 A | 1/1989 | Helbig et al. ................. 384/49 |
| 5,071,264 A | 12/1991 | Franke et al. ................ 384/501 |
| 5,272,776 A | * 12/1993 | Kitamura ........................ 5/601 |
| 5,448,608 A | 9/1995 | Swain et al. ..................... 378/4 |
| 5,477,575 A | * 12/1995 | Lehne et al. .................... 5/601 |
| 5,982,844 A | 11/1999 | Tybinkowski et al. ........... 378/4 |
| 6,044,504 A | * 4/2000 | Stark .............................. 5/601 |
| 6,259,761 B1 | * 7/2001 | Lai ............................... 378/15 |
| 6,314,157 B1 | * 11/2001 | Tachizaki ....................... 378/4 |
| 6,337,894 B1 | 1/2002 | Tybinkowski et al. ........... 378/4 |
| 6,449,331 B1 | * 9/2002 | Nutt et al. ..................... 378/19 |
| 6,490,476 B1 | * 12/2002 | Townsend et al. ........... 600/427 |
| 6,493,571 B1 | * 12/2002 | Bis et al. ..................... 600/420 |

* cited by examiner

*Primary Examiner*—Craig E. Church
*Assistant Examiner*—Jurie Yun
(74) *Attorney, Agent, or Firm*—McDermott, Will & Emery (57) ABSTRACT

A gantry of a combined tomography scanner including an annular outer support, an annular drum concentrically positioned within the outer support rotatable about a rotation axis of the drum, and an annular disk extending radially inwardly from an inner circumferential surface of the drum. At least one of the disk and the drum include structural members for receiving and supporting tomography scanning components on opposing first and second sides of the disk. Among other features and benefits, the gantry can be used for a combined tomography scanner system, e.g., combining an x-ray CT scanner and a PET scanner in a single machine.

29 Claims, 6 Drawing Sheets

GANTRY FOR COMBINED TOMOGRAPHY SCANNER

CROSS-REFERENCE TO RELATED APPLICATIONS

The present application claims priority to co-pending provisional U.S. patent application Ser. No. 60/305,813, which was filed on Jul. 16, 2001, is assigned to the assignee of the present application, and is incorporated herein by reference.

FIELD OF THE INVENTIONS

The present inventions relates generally to tomography systems and, more specifically, to a combined tomography system. Even more specifically, the present inventions are directed to a gantry for a combined tomography system and supports located within a gantry of a combined tomography system for supporting a patient table extending into the gantry.

BACKGROUND OF THE INVENTIONS

X-ray computed tomography (CT) scanners have been used for over twenty-five years to create images of cross-sectional slices of subjects, such as human patients, and are particularly used as a medical diagnostic aid. An x-ray CT scanner can produce a 3-dimensional anatomic image of a patient's body.

An annular gantry normally supports many of the components of an x-ray CT scanner and includes an outer ring secured to a stand and an inner ring mounted for rotation within the outer ring. During a scanning procedure, a patient table is positioned through the center of the gantry and the inner ring is rotated about the table. The components supported by the gantry can include an x-ray tube for providing the x-ray beam, one or more high voltage power supplies, balancing weights, a data acquisition module, and a bank of detectors diametrically opposed from the x-ray source. At least some of these components are secured in the inner ring for rotation therewith.

Positron emissions tomography (PET) scanning is a more recently developed procedure that uses positron emitting radioactive isotopes to show function or metabolism, rather than anatomy as in x-ray CT scanning techniques. A PET scanner is made up of special radiation detectors called scintillators which are arranged in a ring configuration within an annular gantry. Basically, each detector has an associated partner detector oppositely located on the ring. This setup allows for the sensing and measurement of positrons emitted by radioactive isotopes injected into a patient. The measurements are processed through nuclear counting equipment and computers to produce 3-dimensional images that allow quantitation of the physiochemical process in the patient's body. PET scanners are used to diagnose and monitor cancer, in addition to diseases of the heart, brain and lungs.

Recently, the results of different types of scanning procedures, e.g., PET and x-ray CT scans (and MRI and x-ray procedures), have been combined, or superimposed, to take advantage of the particular benefits of each procedure. Accordingly, a patient is first scanned using a first procedure, then scanned using a second procedure, and the results of both scans are combined using specialized software and computing systems.

In order to obtain tomographic images of a patient with either scanner, it is necessary that the patient be located exactly at a predetermined position inside the opening of an annular scan gantry of the apparatus. For this reason, such scanners have been provided with a patient handling couch or table which is moveable vertically to be in line with an axis of the scan gantry, and moveable axially in and out of the scan gantry. Some existing systems includes a patient support couch or table that is movable between two or more separate scanning machines, such as an x-ray CT scanner and a PET scanner.

What is still desired, however, is a new and improved gantry that supports the components of at least two scanning machines, such as an x-ray CT scanner and a PET scanner. In this manner a patient can be successively scanned by two types of scanning machines by simply repositioning the patient in the same gantry.

Since a gantry of a combined tomography system may need to be longer than a typical gantry, and require that a patient table extend further into the gantry during the scanning procedures, what are also desired are new and improved supports located within the gantry of the combined tomography system for supporting the patient table extending into the gantry. The supports will prevent significant deformation (e.g., bending) of the extended patient table, such that a patient on the table can be located exactly at a predetermined position inside the opening of the gantry of the combined tomography system.

SUMMARY OF THE INVENTIONS

The present inventions accordingly generally provide a new and improved gantry that supports the components of at least two scanning machines, such as an x-ray CT scanner and a PET scanner, and new and improved supports located within the gantry of the combined tomography system for supporting a patient table extending into the gantry.

According to one aspect of the present inventions, the gantry includes an annular outer support, an annular drum concentrically positioned within the outer support rotatable about a rotation axis of the drum, and an annular disk extending radially inwardly from an inner circumferential surface of the drum. At least one of the disk and the drum include structural members for receiving and supporting tomography scanning components on opposing first and second sides of the disk. Among other features and benefits, the gantry can be used for a combined tomography scanner system, e.g., combining an x-ray CT scanner and a PET scanner in a single machine.

According to another aspect of the present inventions, a scanner system includes an annular gantry rotatable about a horizontal center of rotation. The system also includes a non-rotating sleeve coaxially positioned within the annular gantry and rollers secured to an inner surface of the sleeve for supporting a patient table pallet extending into the sleeve. Among other features and benefits, the rollers are particularly useful for supporting a patient table extending into a long gantry of a combined tomography system during scanning procedures, e.g., x-ray CT and PET scanning procedures.

The foregoing and other features and advantages of the present inventions will become more readily apparent from the following detailed description of the disclosure, as illustrated in the accompanying drawing.

BRIEF DESCRIPTION OF THE INVENTION

Like reference characters designate identical or corresponding components and units throughout the several views.

DETAILED DESCRIPTION OF EXEMPLARY EMBODIMENTS

Referring first to FIGS. 1 through 5, a combined tomography scanner system 100 is shown with a patient table pallet 102 supported within a gantry (only an outer cover 104 of the gantry is shown) of the system 100 by exemplary embodiments of support members 200 constructed in accordance with the present inventions. Among other features and advantages, the support members 200 of the present inventions prevent significant deformation (e.g., bending) of the extended patient table pallet 102, such that a patient or other sample (not shown) positioned on the pallet 102 can be located exactly at a predetermined position inside the opening of the gantry of the combined tomography system 100.

The support members 200 of the present inventions are especially useful for use in a combined tomography scanner system 100, combining for example an x-ray CT scanner and a PET scanner, since the gantry of such a system is longer that the gantry of a typical single tomography scanner, thereby requiring that the patient table pallet be extended further into the combined scanner. However, the support members 200 of the present inventions are not meant to be limited for use in a combine tomography scanner, and can be used within the gantries of existing single tomography scanners.

The scanner system 100 includes the annular gantry rotatable about a horizontal center of rotation 106. The system 100 also includes a non-rotating sleeve 202 coaxially positioned within the annular gantry and the support members 200 are secured to an inner surface of the sleeve 202 for supporting the patient table pallet 102 extending into the sleeve 202.

Figure 1:
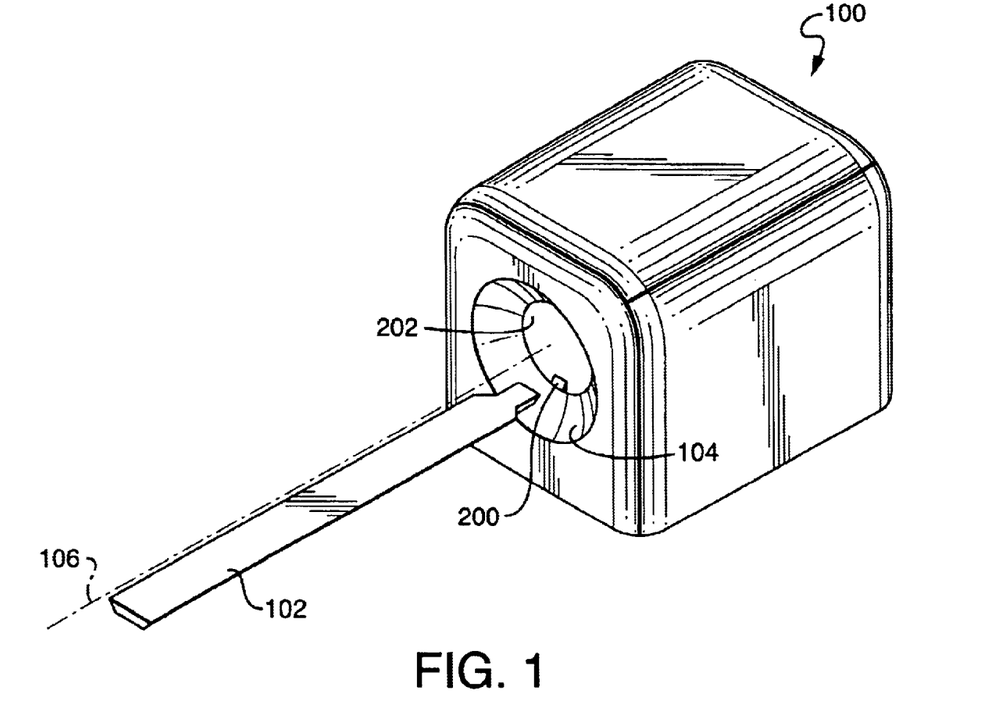
FIG. 1 is a top and end perspective view of an exemplary embodiment of a combined tomography scanner constructed in accordance with the present invention, and a patient table pallet shown positioned for insertion into a gantry of the combined tomography scanner.
Figure 2:
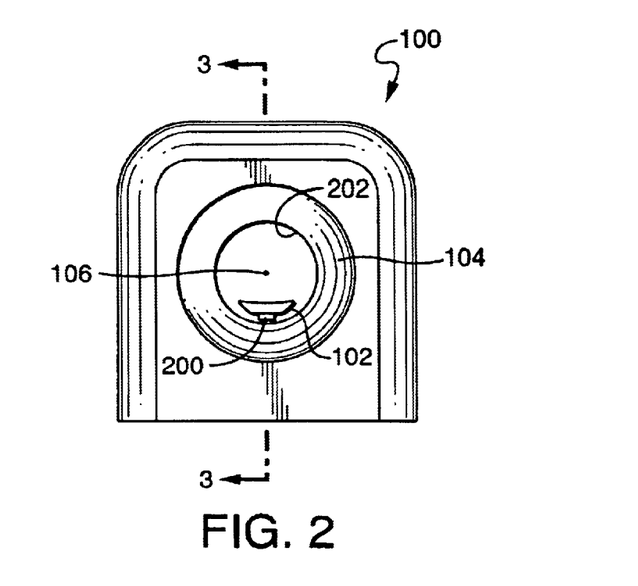
FIG. 2 is a front end elevation view of the combined tomography scanner of FIG. 1, showing the patient table pallet supported within the gantry on an exemplary embodiment of support members constructed in accordance with the present invention.
Figure 3:
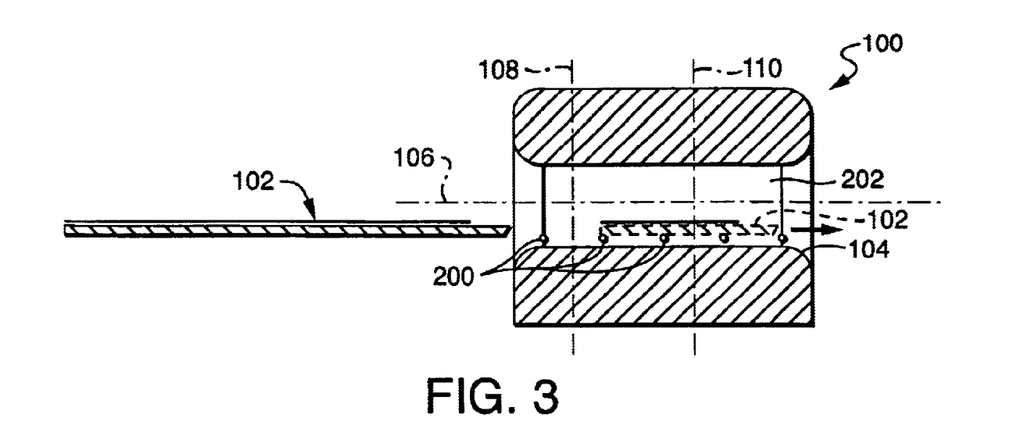
FIG. 3 is a sectional view of the combined tomography scanner and the patient table pallet taken along line 3—3 of FIG. 2.
Figure 4:
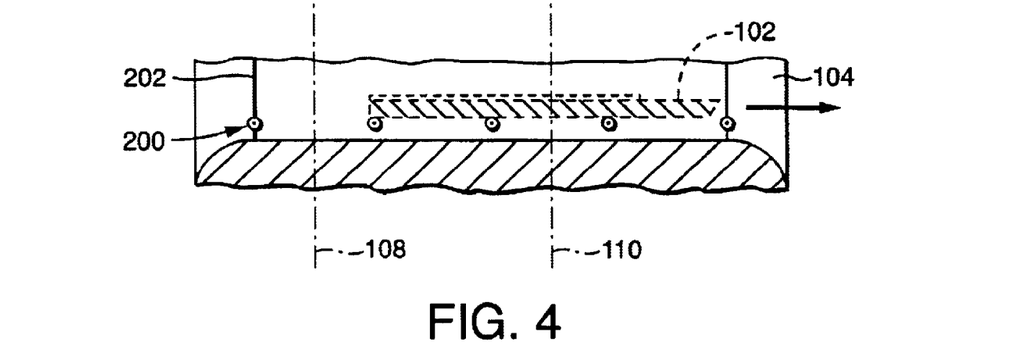
FIG. 4 is an enlarged sectional view of a portion of the combined tomography scanner and the patient table pallet taken along line 3—3 of FIG. 2.
Figure 5:
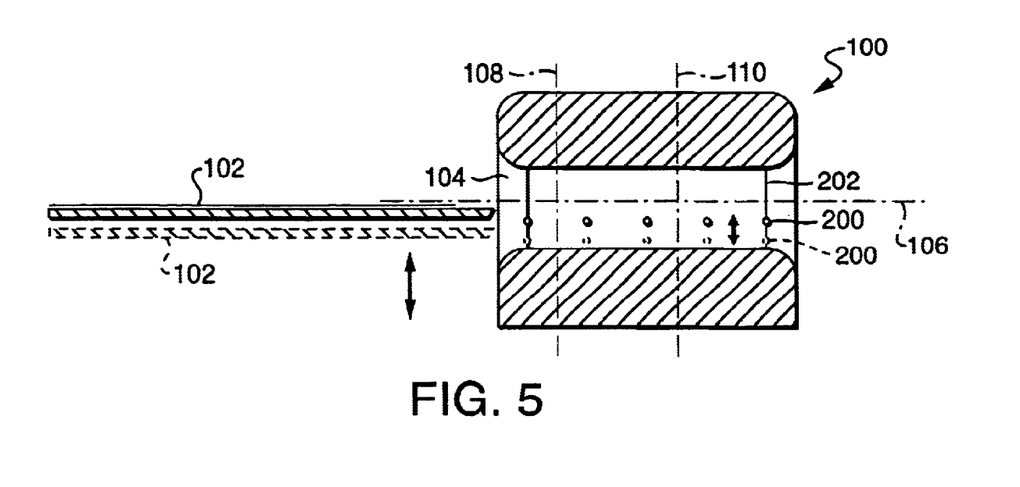
FIG. 5 is a sectional view of the combined tomography scanner showing the support members being vertically adjusted within the gantry of the scanner.

In the exemplary embodiment of FIGS. 1 through 5, the support members comprise rollers 200 that are arranged in a single row extending between a first end and a second end of the sleeve 202. As shown in FIG. 5, the rollers 200 can be provided as vertically movable in order to support the patient table pallet 102 at variable heights within the gantry. The rollers 200 can be vertically adjusted either before or after the patient table pallet 102 is placed on the rollers 200. FIGS. 3 through 5 also illustrate possible scan planes of the scanner system, e.g., an x-ray CT scan plane 110 and a PET scan plane 108.

Referring now to FIGS. 6 through 9, an exemplary embodiment of a frame 10 constructed in accordance with the present inventions is shown. The frame of FIGS. 6 through 8 supports components for performing at least two types of tomography scans, e.g., an x-ray CT scan and a PET scan, and can be used, for example, for the combined tomography scanner of FIGS. 1 through 5. The frame includes a stand 12 and an annular gantry 14 supported on the stand. At least some of the components for performing tomography scans are mounted on the gantry 14 so as to be dynamically balanced about a center of rotation 106 of the gantry.

The gantry 14 includes an annular outer support 16, an annular drum 18 concentrically positioned within the outer support 16, and an annular disk 20 extending radially inwardly from an inner circumferential surface of the drum 18. The disk 20 has a central opening 22 for receiving a patient to be scanned, and the disk 20 is adapted to receive and support computed tomography components, as discussed in greater detail below.

Figure 9:
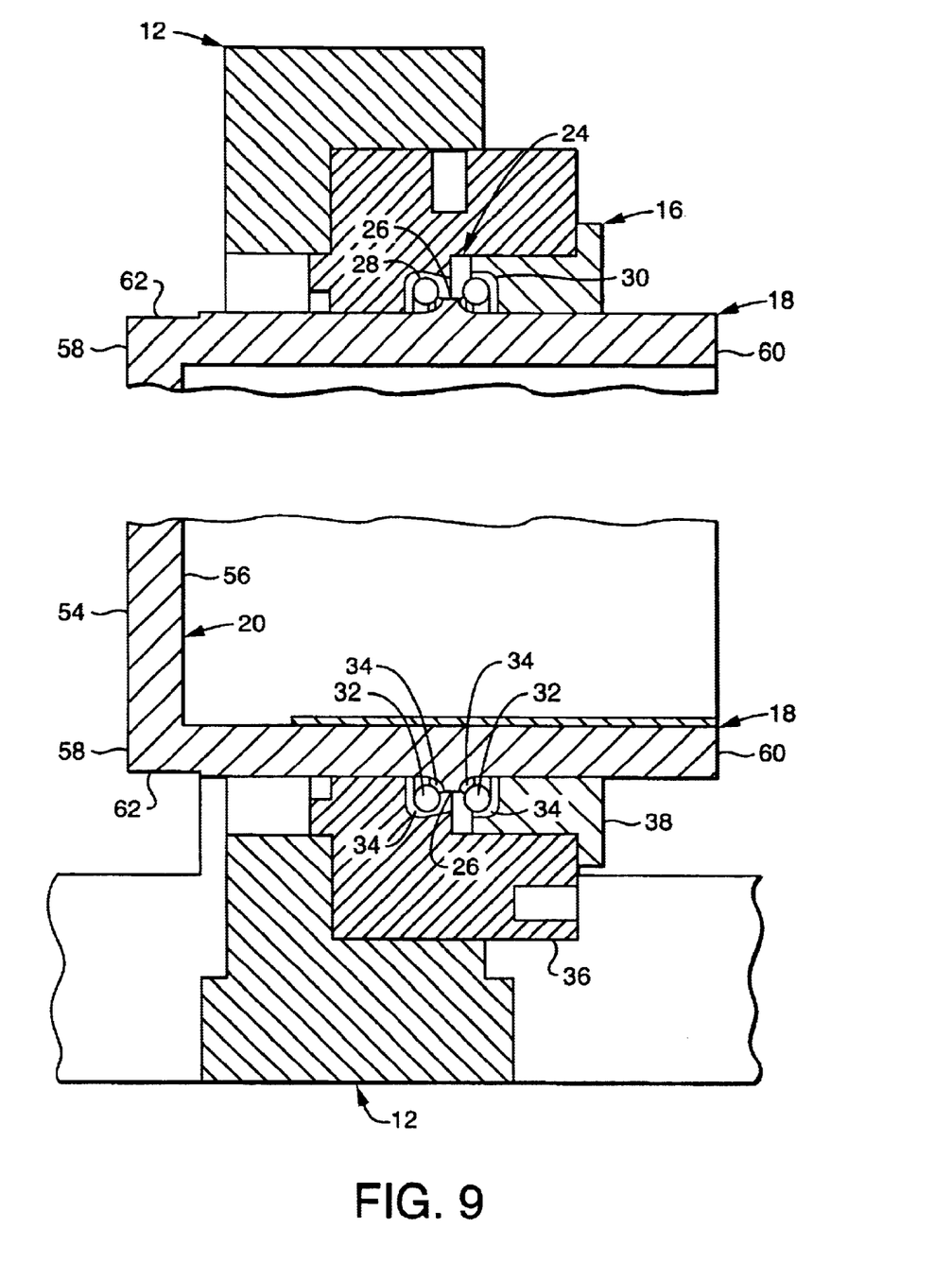
FIG. 9 is an enlarged sectional view of portions of the frame of FIG. 6, showing a rotary bearing assembly of the gantry of the frame.

As shown best in FIG. 9, the annular outer support 16 has a radially inwardly facing, continuous circumferencial bearing chamber 24, and the drum 18 has a continuous circumferential bearing lip 26 radially extending into the bearing chamber 24 of the outer support 16 to define two circumferential bearing runs 28, 30 within the bearing chamber 24. The gantry 14 also includes roller bearings 32 in the bearing runs 28, 30 allowing the drum 18 to rotate within the outer support 16, such that the drum 18 and the disk 20 (and computed tomography components supported on the disk 20) are rotatable about a rotation axis 106 of the drum 18. The rotation axis 106 of the drum 18 coincides with the scan axis of an x-ray CT scanner incorporating the frame.

Preferably, the roller bearings comprise spherical ball bearings 32. Bearing wires 34 are provided and circumferentially extend within the bearing runs 28, 30 and guide the spherical ball bearings. Suspended between the bearing wires 34, the spherical ball bearings 32 glide across the wires with minimal resistance as the drum 18 rotates within the outer support 16. In particular, bearing wires 34 are positioned on either side of the bearing lip 26, and bearing wires are positioned in two circumferential corners of the bearing chamber 24. The bearing arraignment emulates the well-known Franke bearing interface, as disclosed in U.S. Pat. Nos. 4,797,008 and 5,071,264, which are incorporated herein by reference. Ball spacers can be provided between the ball bearings 32 to prevent adjacent balls from contacting or otherwise interfering with each other. The bearings 32 are preloaded according to manufacturer specifications, as described below.

The bearing arrangement is disclosed in U.S. Pat. No. 6,337,894, to Tybinkowski et al., entitled Rotary Bearing Assembly for CT Scanner Gantry, and which is assigned to the assignee of the present application and incorporated herein by reference. The bearing arrangement confers several advantages. First, the bearings 32 and the wire 34 interface operates with less friction than traditional bearing races as the wires provide a smooth and efficient track for the ball bearings. As a result, the bearing arrangement reduces the torque necessary to rotate the drum 18 and the disk 20 within the outer support 16. Also, no custom bearing housing is required, as the bearing runs 28, 30 are provided by the surfaces of the drum 18 and the outer support 16. Furthermore, the bearing arrangement and novel gantry 14 design according to the present disclosure requires fewer parts, are light weight, operate quietly, and are relatively inexpensive.

The annular outer support 16 preferably is constructed from first and second annular pieces 36, 38 axially joined to define the bearing chamber 24. The pieces 36, 38 are secured together with bolts, which pre-load the bearings 32 and are tightened according to the bearing manufacturer's specifications. Although not shown, the annular first piece 36 can include grease fittings providing communication with the bearing chamber 24 so that the ball bearings 32 can be packed in grease in a convenient manner.

Figure 6:
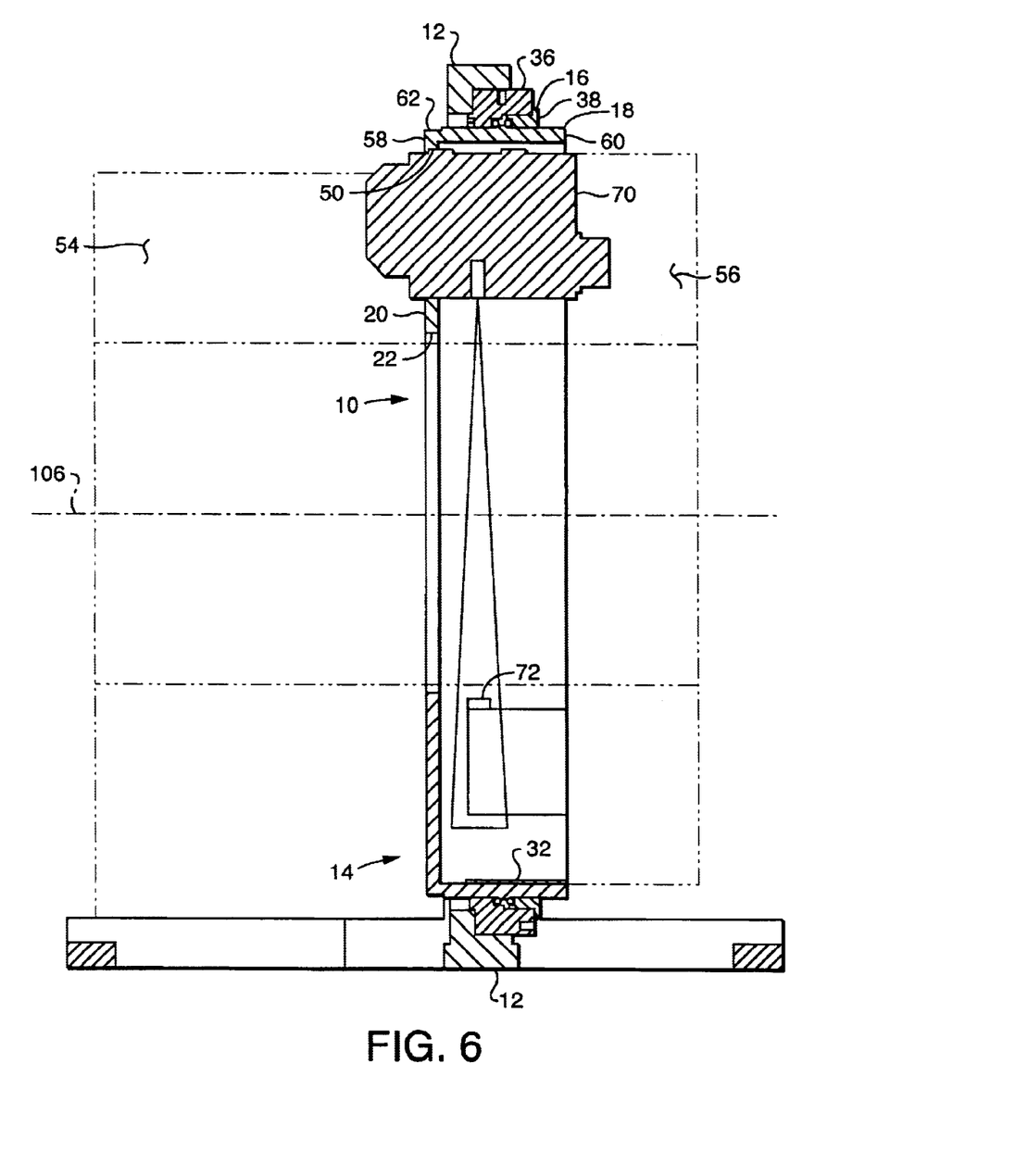
FIG. 6 is an enlarged sectional view of an exemplary embodiment of a frame for a combined tomography scanner constructed in accordance with the present invention, show with x-ray CT scanner components thereon.
Figure 7:
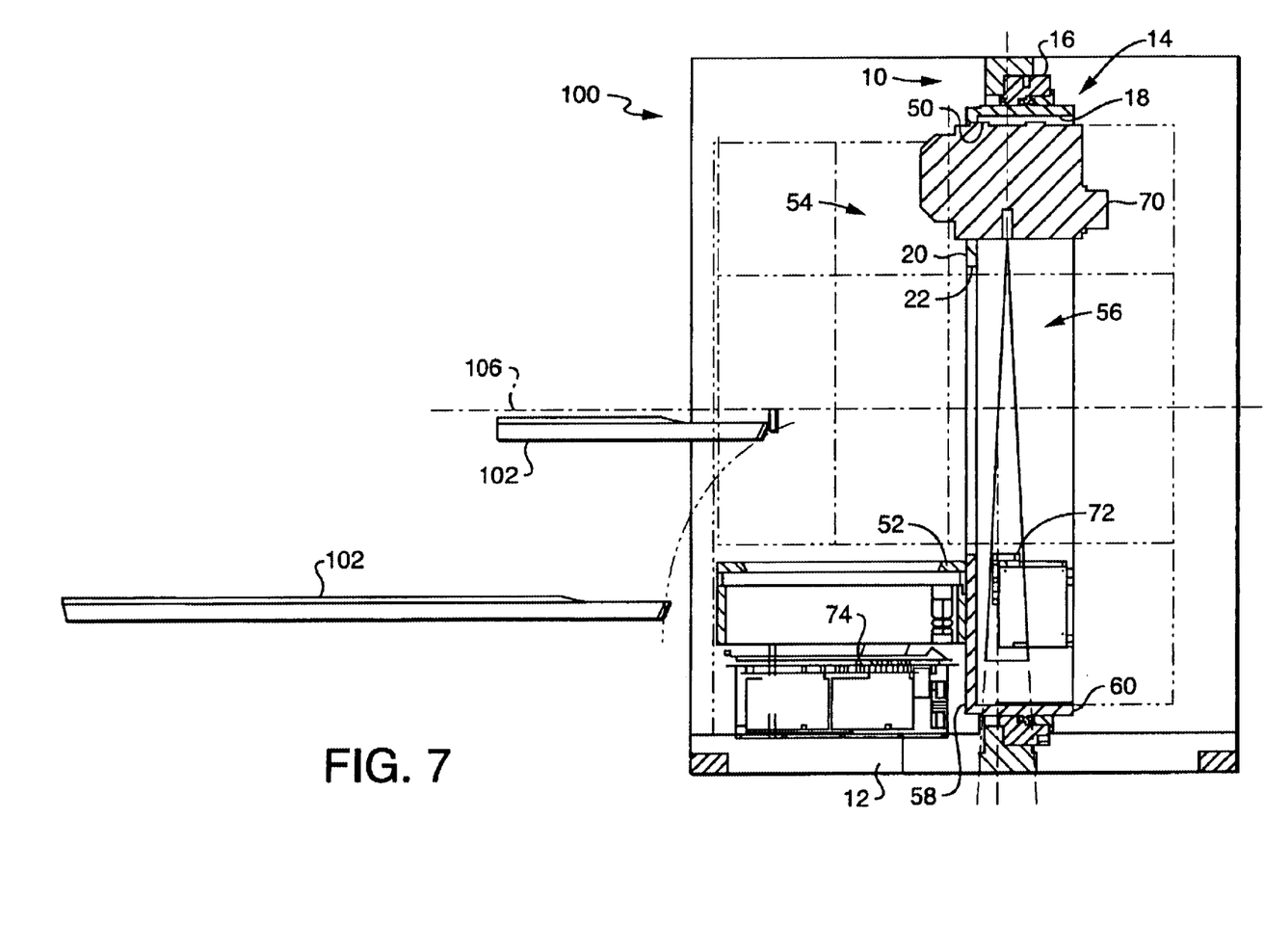
FIG. 7 is a sectional view of the frame of FIG. 6, show with x-ray CT scanner components and PET scanner components mounted thereon, and shown with a patient table pallet being raised for insertion into a gantry of the frame.
Figure 8:
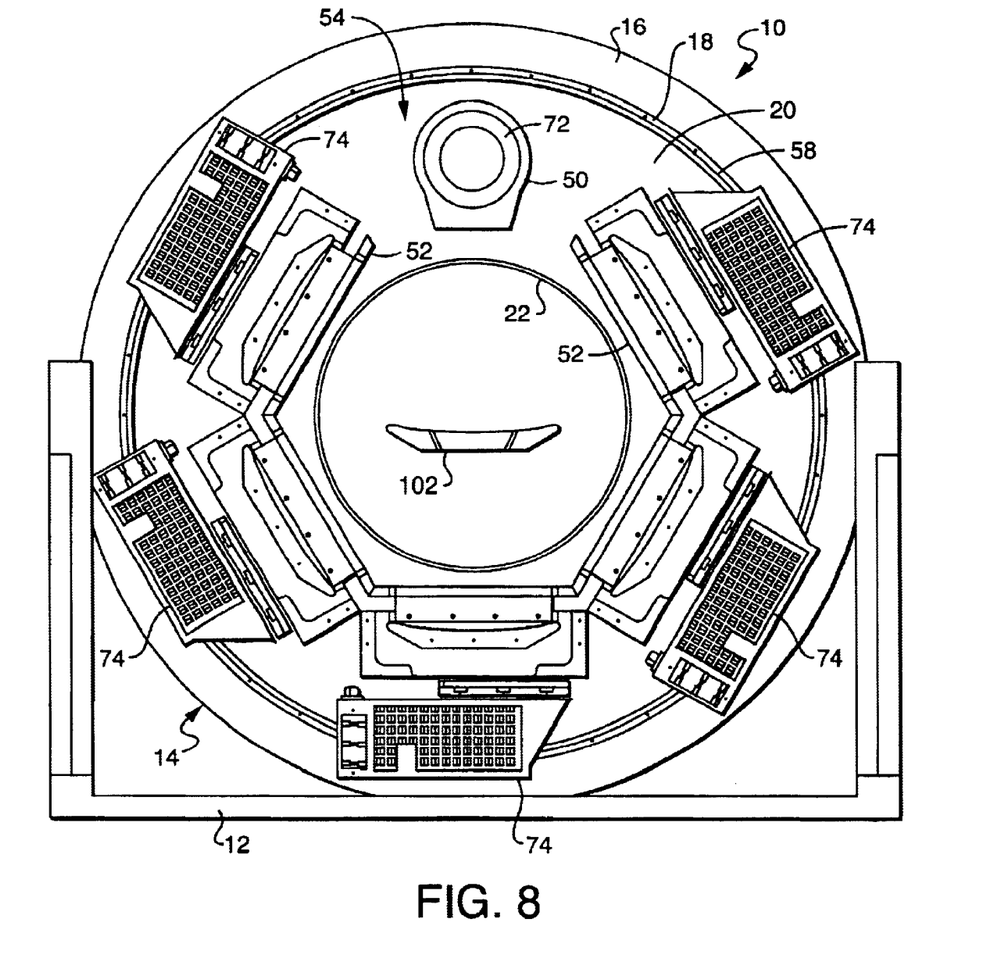
FIG. 8 is a front end elevation view of the frame of FIG. 6, show with x-ray CT scanner components and PET scanner components mounted thereon, and shown with a patient table pallet raised for insertion into the gantry of the frame.

As shown best in FIGS. 6 through 8, at least one of the disk 20 and the drum 18 include various openings 50 and structural members 52 for receiving and supporting tomography scanning components (e.g., an x-ray source 70, an x-ray detector 72, and a scintillators 74) on opposing first and second sides 54, 56 of the disk 20. The components secured to the annular disk 20 will of course rotate with the drum 18 about the rotation axis 106. The disk 20 is preferably adapted such that components mounted thereon will be dynamically balanced about the rotation axis 106 of the disk 20. In particular, the opening 50 and the structural members 52 are provided so that components will be mounted on both sides of the disk 20, and at least some of the components, such as the x-ray source 70, will extend through the disk 20, whereby the components can be dynamically balanced about the rotation axis 106 of the disk 20.

Major components of the two tomography scanners to be mounted on the disk 20 include an x-ray source, a detector array, an x-ray power source including a power converter and batteries, a power source for the detector array, scintillators, and a control and data handling electronics package. Accordingly, the term "components" as used herein can include not only one or more of these major components, but also any number of elements supported by the disk 20, depending upon the particular design(s) of the tomography scanners. For example, a number of minor components in the sense of mass and volume, such as a collimator, a motor driven fan for cooling the x-ray source, anti-scatter plates for the detector array, a detector assembly control panel and/or the like are also typically mounted on the disk 20, and thus can be included in the term "components" as used herein.

The gantry 14 is also adapted so that the weight of the gantry 14 and any components mounted thereon are substantially aligned with the bearings 32. In particular, the drum 18 axially extends between first and second ends 58, 60, and the bearing lip 26 is positioned between the ends and closer to the second end 60 than the first end 58, i.e., the bearing lip 26 is not located at the middle of the drum 18. In addition, the annular disk 20 is not concentrically aligned with the bearing lip 26 of the drum 18, but extends from the first end 58 of the drum 18. By locating the bearings 32 at the center of mass of the gantry 14, a smaller bearing configuration is allowed since the moment arm between the bearings 32 and the center of mass of the disk 20 is minimized, thereby decreasing the radial load and thrust load on the bearings. This, in combination with the mounting of components on both sides of the gantry disk 20, achieves dynamic balancing of the disk 20 relative to the bearings 32, and substantially eliminates cantilevered loading on the bearings 32.

U.S. Pat. No. 5,448,608 to Swain et al., entitled Tomographic Scanner Having Center of Rotation for All Physics, and which is assigned to the assignee of the present application and incorporated herein by reference, discloses an x-ray tomography system wherein components are mounted on a drum so as to be dynamically balanced for rotation with the drum about a rotational axis. The scanner disclosed by Swain et al. is also configured so that the center of the mass moment of inertia, the center of rotation, the center of thermal expansion of the drum and components mounted thereon, and the center of the scanning plane substantially coincident on the rotational axis of the drum.

Preferably, the outer support 16, the drum 18 and the disk 20 of the gantry 14 according to the present disclosure are made of the same light-weight, rigid metal such as aluminum, magnesium-aluminum alloy and the like. The drum 18 and the disk 20 are preferably made as a single piece.

Referring to FIGS. 6, 7 and 9, a portion 62 of the radially outermost surface of the rotatable drum 18 is sheaved to interface with longitudinal grooves of a poly-V-belt (not shown). The cross-sectional V-shaped geometry of the belt in combination with the large drum 18 circumference serve to minimize belt slippage, maximizing accuracy in rotational disk 20 positioning and rotation rate. The sheaved portion 62 is preferably provided adjacent to the first end 58 of the drum 18. Although not shown, the frame 10 can include a motor and drive pulley system and corresponding belt tensioner such as that disclosed in U.S. Pat. No. 5,982,844 to Tybinkowski et al., which is assigned to the assignee of the present disclosure and incorporated herein by reference.

It should be understood that the embodiments of the present inventions described herein are merely exemplary and that a person skilled in the art may make variations and modifications to the embodiments described without departing from the spirit and scope of the present inventions. All such equivalent variations and modifications are intended to be included within the scope of these inventions as defined by the appended claims.

What is claimed is:

1. A gantry adapted for use as part of a combined tomography scanner, the gantry comprising:

an annular outer support;

an annular drum concentrically positioned within the outer support rotatable about a rotation axis of the drum; and an annular disk extending radially inwardly from an inner circumferential surface of the drum;

wherein at least one of the disk and the drum include structural members adapted to receive and support tomography scanning components on opposing first and second sides of the disk, wherein the drum axially extends between first and second ends, and wherein the annular disk extends from the first end of the drum.

2. A gantry according to claim 1, wherein the annular disk includes apertures for receiving tomography scanning components.

3. A gantry according to claim 1, further including a stand supporting the annular outer support.

4. A scanner system including a gantry according to claim 1, and further comprising:
   positron emissions tomography components operatively mounted on the first side of the annular disk of the gantry for rotation therewith about the rotation axis; and
   x-ray computer tomography components operatively mounted on the second side of the annular disk of the gantry for rotation therewith about the rotation axis.

5. A scanner system according to claim 4, wherein at least some of the x-ray computer tomography components extend through the disk.

6. A gantry according to claim 1, wherein the structural members of the disk and the drum are positioned and arranged on the disk and the drum so that components fixedly mounted on the structural members, the disk and the drum will be substantially balanced for rotation with the disk and the drum about the rotation axis.

7. A gantry according to claim 1, wherein the disk, the drum and the outer support are formed of the same lightweight, rigid metal.

8. A gantry adapted for use as part of a combined tomography scanner, the gantry comprising:
   an annular outer support;
   an annular drum concentrically positioned within the outer support rotatable about a rotation axis of the drum; and
   an annular disk extending radially inwardly from an inner circumferential surface of the drum;
   wherein at least one of the disk and the drum include structural members adapted to receive and support tomography scanning components on opposing first and second sides of the disk,
   wherein a portion of the radially outermost surface of the rotatable drum is sheaved.

9. A gantry according to claim 8, further comprising:
   a motor having a sheaved drive pulley; and
   a belt mounted between the sheaved drive pulley and the sheaved portion of the drum.

10. A scanner system including a gantry according to claim 8, and further comprising:
    positron emissions tomography components operatively mounted on the first side of the annular disk of the gantry for rotation therewith about the rotation axis; and
    x-ray computer tomography components operatively mounted on the second side of the annular disk of the gantry for rotation therewith about the rotation axis.

11. A gantry adapted for use as part of a combined tomography scanner, the gantry comprising:
    an annular outer support;
    an annular drum concentrically positioned within the outer support rotatable about a rotation axis of the drum; and
    an annular disk extending radially inwardly from an inner circumferential surface of the drum;
    wherein at least one of the disk and the drum include structural members adapted to receive and support tomography scanning components on opposing first and second sides of the disk,
    wherein the drum and annular disk are unitary.

12. A scanner system including a gantry according to claim 11, and further comprising:
    positron emissions tomography components operatively mounted on the first side of the annular disk of the gantry for rotation therewith about the rotation axis; and
    x-ray computer tomography components operatively mounted on the second side of the annular disk of the gantry for rotation therewith about the rotation axis.

13. A gantry adapted for use as part of a combined tomography scanner, the gantry comprising:
    an annular outer support;
    an annular drum concentrically positioned within the outer support rotatable about a rotation axis of the drum; and
    an annular disk extending radially inwardly from an inner circumferential surface of the drum;
    wherein at least one of the disk and the drum include structural members adapted to receive and support tomography scanning components on opposing first and second sides of the disk, wherein:
       the annular outer support includes a radially inwardly facing, continuous circumferential bearing chamber;
       the annular drum has a continuous circumferential bearing lip radially extending into the bearing chamber of the outer support to define two circumferential bearing runs within the bearing chamber; and
       roller bearings are contained in the bearing runs rotatably supporting the drum within the outer support.

14. A gantry according to claim 13, wherein the drum axially extends between first and second ends, and the bearing lip is positioned between the ends.

15. A gantry according to claim 14, wherein the bearing lip is positioned closer to the second end of the drum.

16. A gantry according to claim 13, wherein the roller bearings comprise spherical ball bearings.

17. A gantry according to claim 13, further comprising bearing wires circumferentially extending within the bearings runs and guiding the roller bearings.

18. A gantry according to claim 17, wherein bearing wires are positioned on either side of the bearing lip, and bearing wires are positioned in two circumferential corners defined by the bearing chamber.

19. A gantry according to claim 13, wherein the annular outer support includes first and second annular pieces axially joined to define the bearing chamber.

20. A gantry according to claim 19, wherein the first and second annular pieces are secured together with preloaded bolts.

21. A gantry according to claim 13, wherein the annular outer support includes grease fittings providing communication with the bearing chamber.

22. A gantry according to claim 13, further comprising:
    a non-rotating sleeve coaxially positioned within the annular gantry; and
    rollers secured to an inner surface of the sleeve for supporting a patient table pallet extending into the sleeve.

23. A gantry according to claim 22, wherein the rollers are arranged in a single row extending between a first end and a second end of the sleeve.

24. A scanner system including a gantry according to claim 13, and further comprising:
    positron emissions tomography components operatively mounted on the first side of the annular disk of the gantry for rotation therewith about the rotation axis; and
    x-ray computer tomography components operatively mounted on the second side of the annular disk of the gantry for rotation therewith about the rotation axis.

25. A gantry adapted for use as part of a combined tomography scanner, the gantry comprising:

an annular outer support;

an annular drum concentrically positioned within the outer support rotatable about a rotation axis of the drum; and an annular disk extending radially inwardly from an inner circumferential surface of the drum, wherein at least one of the disk and the drum include structural members adapted to receive and support tomography scanning components on opposing first and second sides of the disk;

a non-rotating sleeve coaxially positioned within the annular gantry; and rollers secured to an inner surface of the sleeve for supporting a patient table pallet extending into the sleeve, wherein the rollers are vertically movable.

26. A scanner system including a gantry according to claim 25, and further comprising:

positron emissions tomography components operatively mounted on the first side of the annular disk of the gantry for rotation therewith about the rotation axis; and x-ray computer tomography components operatively mounted on the second side of the annular disk of the entry for rotation therewith about the rotation axis.

27. A tomography scanner system comprising:

an annular gantry rotatable about a horizontal center of rotation;

positron emissions tomography components operatively mounted on a first side of the gantry for rotation therewith about the center of rotation;

x-ray computer tomography components operatively mounted on a second side of the gantry for rotation therewith about the center of rotation;

a non-rotating sleeve coaxially positioned within the annular gantry; and rollers secured to an inner surface of the sleeve for supporting a patient table pallet extending into the sleeve, wherein the rollers are vertically movable.

28. A scanner system according to claim 27, wherein the rollers are arranged in a single row extending between a first end and a second end of the sleeve.

29. A scanner system according to claim 28, wherein the gantry contains an x-ray source for projecting a beam of x-rays across the center of rotation to a detector array on an opposite side of the gantry.

* * * * *